United States Patent [19]

Farnham

[11] 4,447,628

[45] May 8, 1984

[54] NONHYGROSCOPIC, ANIONIC PENTACOORDINATE SILICATE

[75] Inventor: William B. Farnham, Wilmington, Del.

[73] Assignee: E. I. Du Pont de Nemours and Company, Wilmington, Del.

[21] Appl. No.: 397,212

[22] Filed: Jul. 12, 1982

[51] Int. Cl.$^3$ ............... C07F 7/08; C07F 7/10; C07F 7/18

[52] U.S. Cl. .................. 556/415; 556/464; 260/349; 526/89; 526/128; 526/194

[58] Field of Search ............... 556/415, 464; 260/349

[56] References Cited

U.S. PATENT DOCUMENTS

| | | | |
|---|---|---|---|
| 3,355,477 | 11/1967 | Frye | 556/464 |
| 3,360,525 | 12/1967 | Frye | 556/464 X |
| 3,455,980 | 7/1969 | Frye | 556/464 X |
| 3,508,946 | 4/1970 | Plueddemann et al. | 556/464 X |
| 3,555,069 | 1/1971 | Frye | 556/464 X |

OTHER PUBLICATIONS

Clark, Chem. Rev. 80, 429, (1980).
Farnham et al., J. Am. Chem. Soc. 103, 4808, (1981).
Perrozzi et al., J. Am. Chem. Soc. 101, 1591, (1979).

*Primary Examiner*—Paul F. Shaver

[57] ABSTRACT

Nonhygroscopic, anionic pentacoordinate silicate, for example,

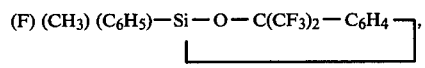

soluble in commonly used organic solvents, and useful as a source of fluoride, cyanide or azide anion and as a catalyst or cocatalyst in polymerization systems, for example, the polymerization of methyl methacrylate.

7 Claims, No Drawings

NONHYGROSCOPIC, ANIONIC PENTACOORDINATE SILICATE

DESCRIPTION

1. Field of the Invention

This invention relates to pentacoordinate silicates which serve as anhydrous anion sources and which are useful as polymerization catalysts and cocatalysts.

2. Background

Clark in Chem. Rev. 80, 429 (1980) includes in a discussion of the fluoride ion as a base in organic synthesis a review of organic and inorganic fluoride sources. Many of these have limited or no solubility in organic solvents and are difficult or impossible to maintain in the anhydrous state because of their hygroscopic nature.

Farnham et al. in J. Am. Chem. Soc. 103, 4608 (1981) discuss structural aspects of the anionic pentacoordinate silicon compounds of the formulae

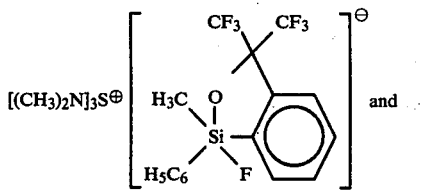

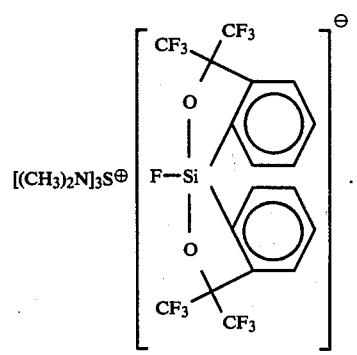

Perrozzi et al. in J. Am. Chem. Soc. 101, 1591 (1979) disclose similar pentacoordinate silicon compounds of the formula

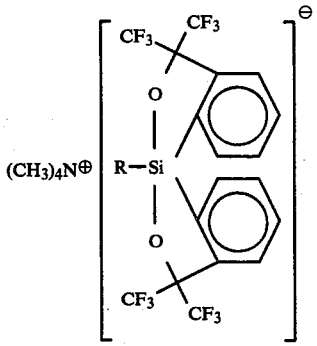

wherein R is methyl or phenyl.

It is an object of this invention to provide an anhydrous, nonhygroscopic, thermally stable, pentacoordinate silicon compound which can provide a fluoride, cyanide or azide anion. Another object is to provide such an anion source which is useful as a catalyst or cocatalyst in polymerization systems. Still another object is to provide a polymerization system utilizing the aforesaid anion source. A further object is to provide a process for polymerizing methyl methacrylate by means of the aforesaid anion source. Another object is to provide such an anion source which is soluble in commonly used organic solvents. Other objects will become apparent hereinafter.

DISCLOSURE OF INVENTION

For further comprehension of the invention and of the objects and advantages thereof, reference may be made to the following description and to the appended claims in which the various novel features of the invention are more particular set forth.

The invention resides in nonhygroscopic, anionic, pentacoordinate silicates which can readily be rendered anhydrous and which are especially suitable for use in nonaqueous solvents, particularly as polymerization catalysts and cocatalysts for acrylate monomers, especially methyl methacrylate. More specifically, the invention resides in compounds of the formula

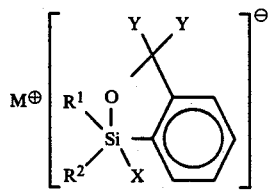

wherein
$R^1$ and $R^2$ are both aryl or one is aryl and the other is $C_{1-4}$ alkyl, or $R^1$ and $R^2$ taken together are

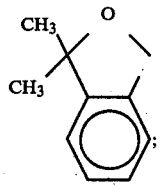

Y is $CF_3$ or, when $R^1$ and $R^2$ are taken together, $CH_3$;
X is F, CN or $N_3$ when Y is $CF_3$;
X is F when Y is $CH_3$;
$M^\oplus$ is $(R^3)_4N^\oplus$, $[(R^4)_2N]_3S^\oplus$ or $Cs^\oplus$ when X is F;
$M^\oplus$ is $(R^5)_4N^\oplus$ when X is CN;
$M^\oplus$ is $[(R^4)_2N]_3S^\oplus$ or $(R^5)_4N^\oplus$ when X is $N_3$;
aryl is phenyl, phenyl substituted with F or $C_{1-4}$ alkyl, $C_{1-4}$ alkoxy or naphthyl;
$R^3$ is $C_{1-4}$ alkyl;
$R^4$ is $C_{1-2}$ alkyl or $(R^4)_2$ is $-CH_2-$5; and
$R^5$ is $C_{2-4}$ alkyl.

The pentacoordinate silicon compounds of this invention are prepared from tetracoordinate silicon precursors. The latter can be prepared by known techniques, such as the following. Hexafluorocumyl alcohol can be converted readily to the dilithium salt, as demonstrated in the examples, for example, by means of tetramethylethylenediamine and n-butyllithium, and then reacted with the dichlorosilane of the formula $R^1R^2SiCl_2$ wherein $R^1$ and $R^2$ are as defined above. The reaction conveniently is carried out in a solvent, for example, tetrahydrofuran, petroleum ether, or a mixture thereof, at a temperature within the range −78° to 25° C. the tetracoordinate cyclic silane which is thus produced can be converted to the desired pentacoordinate silicon compound by means of an appropriate salt which provides M⊕ and X in the aforesaid formula for the compound of the invention. For example, as demonstrated in the examples, such moieties are provided by tris(dimethylamino)sulfonium trimethyldifluorosilicate

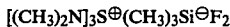
[(CH$_3$)$_2$N]$_3$S$^⊕$(CH$_3$)$_3$Si$^⊖$F$_2$ which is known from U.S. Pat. No. 3,940,402. The reaction conveniently is carried out at room temperature in a solvent, such as acetonitrile or tetrahydrofuran. The simplified nomenclature used in this specification is defined by means of the formulae shown:

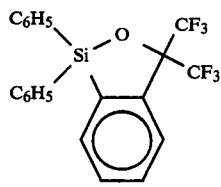

1,1-diphenyl-3,3-bis[trifluoromethyl]-1,3-dihydro-2,1-benzoxasilole

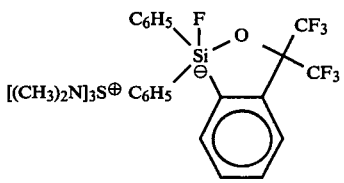

1,1-diphenyl-1-fluoro-3,3-bis[trifluoromethyl]-1,3-dihydro-2,1-benzoxasilole[ion 1-], tris[dimethylamino]-sulfonium salt.

The following examples demonstrate the preparation of pentacoordinate silicates of this invention. All temperatures are in degrees Celsius. Symbols used to describe substituents are the same as those shown in the aforesaid formula.

EXAMPLE 1

A. Cyclic Silane

A solution of α,α-bis(trifluoromethyl)benzyl alcohol (C$_6$H$_5$—C(CF$_3$)$_2$OH: 8.76 g, 35.9 mmol) and tetramethylethylenediamine (TMEDA; 5.41 g, 35.9 mmol) in petroleum ether (70 mL) was treated slowly with butyllithium at ca. 20°. After the addition was complete, the mixture was heated to gentle reflux for 12 h, then cooled to −25°; the resultant dianion of the formula

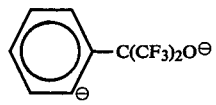

was treated dropwise with a solution of methylphenyldichlorosilane (6.69 g, 35.9 mmol) in petroleum ether (50 mL). The resultant mixture was allowed to warm to 25°, stirred for 18 h, cooled and treated with water. Ether was added and the organic layer was separated and washed with water, brine, dried (MgSO$_4$) and concentrated. Kugelrohr distillation gave a major fraction which solidified (6.44 g). Recrystallization (twice from petroleum ether) gave 4.00 g of white solid, mp 60°-62°. $^{19}$F nmr: $\phi = -75.26$ and $-75.90$ (A$_3$B$_3$, J$_{FF}$=9.0 Hz). $^1$H nmr: $\delta^{TMS}_{CDCl_3}$ 7.85-7.00 (m), 0.70 (s). $^{29}$Si nmr: +24.23 ppm. Anal. Calcd. for C$_{16}$H$_{12}$F$_6$OSi: C, 53.04; H, 3.34. Found: C, 53.24; H, 3.31. These experimental details and the above data confirm that the product compound is the cyclic silane of the formula

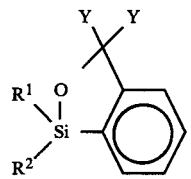

wherein
R$^1$ is methyl, R$^2$ is phenyl and Y is CF$_3$.

B. Fluorosilicate

A mixture of cyclic silane prepared as in Part A (3.94 g) and acetonitrile (20 mL) was treated with 2.89 g of tris(dimethylamino)sulfonium trimethyldifluorosilicate

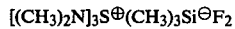
[(CH$_3$)$_2$N]$_3$S$^⊕$(CH$_3$)$_3$Si$^⊖$F$_2$ and stirred for 1.0 h. Volatiles were removed under a stream of nitrogen and the residue was treated with ether. The solid was filtered, washed with ether, and dried to give 5.78 g of white crystals, mp 78°-80° (dec.). $^1$H nmr: $\delta^{TMS}_{CD_3CN}$ 8.10-7.95 (m, 1H), 7.88-7.70 (m, 2H), 7.58-7.00 (m, 6H), 2.72 (s, 18H), 0.14 (s, 3H). $^{19}$F nmr: $\phi = -74.16$ and $-75.19$ (A$_3$B$_3$, J=9.5 Hz). $^{29}$Si nmr: −75.13 (s). Anal. Calcd. for C$_{22}$H$_{30}$N$_3$F$_7$OSSi: C, 48.42; H, 5.54; N, 7.70. Found: C, 47.76; H, 5.49; N, 8.06. These experimental details and the above data confirm that the product compound is the fluorosilicate of the invention and of the aforesaid formula wherein R$^1$ is methyl, R$^2$ is phenyl, X is F, Y is CF$_3$ and M$^⊕$ is [(R$^4$)$_2$N]$_3$S$^⊕$ wherein R$^4$ is methyl.

C. Cyanosilicate

A mixture of tetraethylammonium cyanide (1.16 g, 7.43 mmol) in tetrahydrofuran (10 mL) was treated with a solution of cyclic silane prepared as in Part A (2.69 g, 7.43 mmol) in tetrahydrofuran (10 mL) and stirred for 18 h under a nitrogen atmosphere. Removal of solvent provided a viscous oil which slowly solidified to a brown solid. $^1$H nmr: $\delta^{TMS}_{CD_3CN}$ 8.69-8.35 (m, 1H), 8.00-6.90 (m, 8H), 3.08 (q, J=7 Hz, 8H), 1.10 (doublet of triplets, J$_{HH}$=7 Hz, 12H), 0.63 (s, 3H). These experimental details and the above data confirm that the product compound is the cyanosilicate of the invention and of the aforesaid formula wherein R$^1$ is methyl, R$^2$ is phenyl, X is CN, Y is CF$_3$ and M$^⊕$ is (R$^5$)$_4$N$^⊕$ wherein R$^5$ is ethyl.

EXAMPLE 2

A. Cyclic Silane

The dilithium salt of α,α-bis(trifluoromethyl)-benzyl alcohol was prepared on a 0.20 mol scale by the procedure described in Example 1A. A solution of diphenyldichlorosilane (50.6 g, 0.20 mol) in petroleum ether (100 mL) was added dropwise to the mixture at ca. −50°. After the mixture warmed to 25°, it was heated to 40° for 1.5 h. Ether (250 mL) was added and reflux was continued for 1.0 h. The cooled mixture was treated with water, separated, and dried. Solvent was removed under reduced pressure. Petroleum ether was added and the mixture was filtered and evaporated to give an oil which was kugelrohr distilled to give 10.1 g of oil, bp 140°–150° (0.2 mm). The product slowly crystallized and was recrystallized (hexane), mp 84°–86°. $^1$H nmr: $\delta^{TMS}_{CDCl_3}$ 7.90–7.15 (m). $^{19}$F nmr: $\phi = -75.94$ (s). These experimental details and the above data confirm that the product compound is the cyclic silane of the formula shown in Example 1A wherein $R^1$ and $R^2$ are phenyl and Y is $CF_3$.

B. Fluorosilicate

A solution of cyclic silane prepared as in Part A (1.58 g) in acetonitrile (6 mL) was treated with tris(dimethylamino)sulfonium trimethyldifluorosilicate (1.01 g) and stirred for 1.0 h. Most of the solvent was removed under a stream of nitrogen. Addition of ether, followed by filtration, gave 2.02 g of white crystals, mp 117°–118°. $^1$H nmr: $\delta^{TMS}_{CD_3CN}$ 8.43–8.28 (m, 1H), 8.17–7.87 (m, 4H), 7.75–7.20 (m, 9H), 2.77 (s, 18H). $^{19}$F nmr: $\phi = -107.3$ (s, 1F), $-74.1$ (s, 6F). Anal. Calcd. for $C_{27}H_{32}N_3F_7OSSi$: C, 53.36; H, 5.31; N, 6.91. Found: C, 53.14; H, 5.31; N, 6.92. These experimental details and the above data confirm that the product compound is the fluorosilicate of the invention and of the aforesaid formula wherein $R^1$ and $R^2$ are phenyl, X is F, Y is $CF_3$ and $M^\oplus$ is $[(R^4)_2N]_3S^\oplus$ wherein $R^4$ is methyl.

C. Cyanosilicate

A solution of cyclic silane prepared as in Part A (948 mg) in tetrahydrofuran (THF) (5 mL) was treated with tetraethylammonium cyanide and the mixture was stirred for 2.5 h. The solid was filtered, washed with THF, and dried under vacuum. $^1$H nmr: $\delta^{TMS}_{CD_3CN}$ 8.87–8.67 (m, 1H), 8.00–7.07 (m, 13H), 3.10 (q, J=7 Hz), 1.12 (t with additional coupling to N). $^{19}$F nmr: $\phi = -74.4$ (s). Anal. Calcd. for $C_{30}H_{34}N_2F_6OSi$: C, 62.05; H, 5.90; N, 4.82. Found: C, 61.95; H, 6.25; N, 5.27. These experimental details and the above data confirm that the product compound is the cyanosilicate of the invention and of the aforesaid formula wherein $R^1$ and $R^2$ are phenyl, X is CN, Y is $CF_3$ and $M^\oplus$ is $(R^5)_4N^\oplus$ wherein $R^5$ is ethyl.

D. Azidosilicate

Tris(dimethylamino)sulfonium azide (245 mg, 1.19 mmol) and the cyclic silane prepared as in Part A (500 mg, 1.19 mmol) were dissolved in acetonitrile (1.0 mL). After standing for 0.75 h the solvent was removed under vacuum to give a white solid, mp 113°–115° (dec.). IR featured a strong band at 2050 cm$^{-1}$. $^1$H nmr: $\delta^{TMS}_{CD_3CN}$ 8.22–8.06 (m, 1H), 7.85–7.25 (m, 13H), 2.82 (s, 18H). $^{19}$F nmr: $\phi = -75.0$. Anal. Calcd. for $C_{27}H_{32}N_6F_6OSSi$: C, 51.41; H, 5.11; N, 13.32. Found: C, 51.32; H, 4.95; N, 12.94. These experimental details and the above data confirm that the product compound is the azosilicate of the invention and of the aforesaid formula wherein $R^1$ and $R^2$ are phenyl, X is $N_3$, Y is $CF_3$ and $M^\oplus$ is $[(R^4)_2N]_3S^\oplus$ wherein $R^4$ is methyl.

EXAMPLE 3

A. Cyclic Silane

A solution of α,α-dimethylbenzyl alcohol (50 mmol) and tetramethylethylenediamine (100 mmol) in petroleum ether (100 mL) was treated with butyllithium (100 mmol) at 20°, and the resulting mixture was heated to reflux for 12 h under an atmosphere of argon. The mixture was cooled, treated dropwise with a solution of silicon tetrachloride (25 mmol) in petroleum ether (50 mL), and stirred at 25° for 18 h. The mixture was cooled, treated with water, and extracted with ether. The organic layer was washed with water, dried, and evaporated. Kugelrohr distillation provided 1.90 g of solid material which was recrystallized from petroleum ether. $^1$H nmr: $\delta^{TMS}_{CDCl_3}$ b 7.60–7.20 (m, 8H), 1.68 (s, 12H). These experimental details and the above data confirm that the product compound is the cyclic silane of the formula shown in Example 1A wherein $R^1$ and $R^2$ taken together are

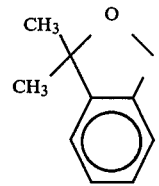

and Y is $CH_3$.

B. Fluorosilicate

A mixture of cyclic silane prepared as in Part A (1.76 g, 6.68 mmol) and acetonitrile (10 mL) was treated with tris(dimethylamino)sulfonium trimethyldifluorosilicate (1.75 g, 6.36 mmol) and stirred for 0.5 h. Solvent was removed under a stream of nitrogen, and the residue was treated with ether, filtered, and washed with ether to give a white solid, mp 115°–123°. $^1$H nmr: $\delta^{TMS}_{CD_3CN}$ 8.00 (m, 2H), 7.28–7.08 (m, 6H), 2.70 (s, 18H), 1.49 (s, 12H). $^{19}$F nmr: $\phi = -115.2$ (s). Anal. Calcd. for $C_{24}H_{38}N_3FO_2SSi$: C, 60.09; H, 7.98; N, 8.76. Found: C, 58.20; H, 7.88; N, 9.03. These experimental details and the above data confirm that the product compound is the fluorosilicate of the invention and of the aforesaid formula wherein $R^1$ and $R^2$ taken together are

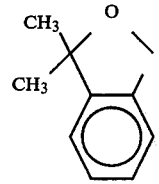

X is F, Y is $CH_3$ and $M^\oplus$ is $[(R^4)_2N]_3S^\oplus$ wherein $R^4$ is methyl.

The utility of the nonhygroscopic, anionic, pentacoordinate silicates of this invention as polymerization catalysts is demonstrated by the following experiments wherein methyl methacrylate is polymerized. To obtain the best polymerization results, the components used for the polymerization reactions generally should be of high purity and free of water and other protic materials. In the following experiments the tetrahydrofuran was distilled from sodium/benzophenone; the dimethylketene methyltrimethylsilylacetal was distilled using a spinning band column; and the methyl methacrylate was purified by passing through a column of neutral alumina.

Experiment 1

A. A solution of the fluorosilicate, in tetrahydrofuran (20 mg in 30 mL), prepared as in Example 2B, at 5° C. was admixed with dimethylketene methyltrimethylsilylacetal (0.35 mL, 2.15 mmol) and methyl methacrylate (5.00 mL, 47 mmol). The reaction mixture was allowed to warm to ca 35° C. After the exotherm had subsided and the temperature was 25° C., the mixture was stirred for 3 h. Methanol was added and solvent was removed under vacuum to yield 5.80 g of white solid polymethyl methacrylate which exhibited $\overline{M}_w = 2530$ and $\overline{M}_n = 2120$ by gel permeation chromatographic (GPC) analysis.

B. A solution of methyl methacrylate (5.0 mL, 47 mmol) and dimethylketene methyltrimethylsilylacetal (0.70 mL, 4.3 mmol) in tetrahydrofuran (15 mL) at 5° C. was treated with the fluorosilicate prepared as in Example 2B (35 mg). The reaction temperature was allowed to reach 60° C. The mixture was stirred at 25° C. for 1.0 h after the exotherm had subsided. Another portion of methyl methacrylate (3.0 mL) was added, and the mixture was stirred for 1.0 h after the exotherm had subsided. The process was repeated twice more, adding a total of 14.0 mL of methyl methacrylate. Methanol was added and solvent was removed under vacuum to yield 16.2 g of white polymethyl methacrylate which exhibited $\overline{M}_w = 3880$ and $\overline{M}_n = 3510$ by GPC analysis.

Experiment 2

A solution of dimethylketene methyltrimethylsilylacetal in tetrahydrofuran (0.70 mL, 4.3 mmol in 15 mL THF) was admixed with the cyanosilicate (38 mg) prepared as in Example 2C. Methyl methacrylate (5.00 mL, 47 mmol) was added and the mixture was stirred for 1.0 h after the exotherm had subsided. Another portion of methyl methacrylate (3.0 mL) was added and the mixture was stirred for 18 h and then processed as in Experiment 1. The yellow solid polymethyl methacrylate which was recovered (9.0 g) exhibited $\overline{M}_w = 2410$ and $\overline{M}_n = 1980$ by GPC analysis.

Experiment 3

A solution of the azidosilicate, in tetrahydrofuran (50 mg in 15 mL), prepared as in Example 2D, was admixed with dimethylketene methyltrimethylsilylacetal (0.70 mL) and methyl methacrylate (5 mL). Following the procedure described in Experiment 1, after stirring for 18 h the reaction mixture was worked up and 2.35 g of solid polymethyl methacrylate was recovered.

Best Mode for Carrying out the Invention

As presently contemplated, the best mode for carrying out the invention is demonstrated by the fluorosilicate of Example 2B and the preceding experiments.

Industrial Applicability

The industrial applicability of the nonhydroscopic, anionic, pentacoordinate silicates of this invention as polymerization catalysts has been demonstrated in the immediately-preceding experiments.

Although the above description includes preferred embodiments of the invention, it is to be understood that there is no intent to limit the invention to the precise constructions herein disclosed and that the right is reserved to all changes and modifications coming within the scope of the invention as defined in the appended claims.

I claim:

1. Nonhygroscopic, anionic, pentacoordinate silicate of the formula

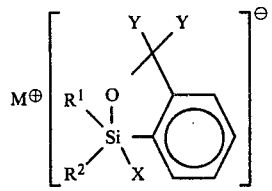

wherein $R^1$ and $R^2$ are both aryl or one is aryl and the other is $C_{1-4}$ alkyl, or $R^1$ and $R^2$ taken together are

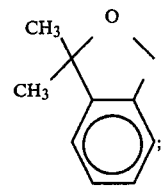

Y is $CF_3$ or, when $R^1$ and $R^2$ are taken together, $CH_3$;

X is F, CN or $N_3$ when Y is $CF_3$;

X is F when Y is $CH_3$;

$M^\oplus$ is $(R^3)_4N^\oplus$, $[(R^4)_2N]_3S^\oplus$ or $Cs^\oplus$ when X is F;

$M^\oplus$ is $(R^5)_4N^\oplus$ when X is CN;

$M^\oplus$ is $[(R^4)_2N]_3S^\oplus$ or $(R^5)_4N^\oplus$ when X is $N_3$;

aryl is phenyl, phenyl substituted with F or $C_{1-4}$ alkyl, $C_{1-4}$ alkoxy or naphthyl;

$R^3$ is $C_{1-4}$ alkyl;

$R^4$ is $C_{1-2}$ alkyl or $(R^4)_2$ is $-CH_2-5$; and $R^5$ is $C_{2-4}$ alkyl.

2. Silicate of claim 1 wherein, in the formula, $R^1$ is methyl, $R^2$ is phenyl, X is F, Y is $CF_3$ and $M^\oplus$ is $[(R^4)_2N]_3S^\oplus$ wherein $R^4$ is methyl.

3. Silicate of claim 1 wherein, in the formula, $R^1$ is methyl, $R^2$ is phenyl, X is CN, Y is $CF_3$ and $M^\oplus$ is $(R^5)_4N^\oplus$ wherein $R^5$ is ethyl.

4. Silicate of claim 1 wherein, in the formula, $R^1$ and $R^2$ are both phenyl, X is F, Y is $CF_3$ and $M^\oplus$ is $[(R^4)_2N]_3S^\oplus$ wherein $R^4$ is methyl.

5. Silicate of claim 1 wherein, in the formula, $R^1$ and $R^2$ are both phenyl, X is CN, Y is $CF_3$ and $M^\oplus$ is $(R^5)_4N^\oplus$ wherein $R^5$ is ethyl.

6. Silicate of claim 1 wherein, in the formula, $R^1$ and $R^2$ are both phenyl, X is $N_3$, Y is $CF_3$ and $M^\oplus$ is $[(R^4)_2N]_3S^\oplus$ wherein $R^4$ is methyl.

7. Silicate of claim 1 wherein, in the formula, $R^1$ and $R^2$ are taken together and are

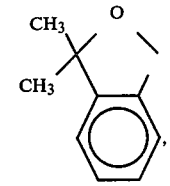

X is F, Y is $CH_3$ and $M^\oplus$ is $[(R^4)_2N]_3S^\oplus$ wherein $R^4$ is methyl.

* * * * *

UNITED STATES PATENT AND TRADEMARK OFFICE
CERTIFICATE OF CORRECTION

PATENT NO. : 4,447,628
DATED : May 8, 1984
INVENTOR(S) : William B. Farnham

It is certified that error appears in the above—identified patent and that said Letters Patent is hereby corrected as shown below:

Column 2, line 16, "particular" should read --particularly--.

Column 2, line 53 and column 8, line 34, "or $C_{1-4}$ alkyl," each occurrence, should read --, $C_{1-4}$ alkyl or--.

Column 2, line 56 and column 8, line 38, "$-CH_2-_5$;" each occurrence, should read -- $(CH_2)_5$;--.

Column 3, line 1, "the", second occurrence, should read --The--.

Column 4, line 32, "IMS" should read --TMS--.

Signed and Sealed this

Twelfth Day of February 1985

[SEAL]

Attest:

DONALD J. QUIGG

Attesting Officer    Acting Commissioner of Patents and Trademarks